United States Patent [19]

Simon et al.

[11] Patent Number: 5,312,986
[45] Date of Patent: May 17, 1994

[54] HEXACARBOXYLIC ACID HEXA-AMIDES WHICH FORM LIPHOPHILIC COMPLEXES WITH MAGNESIUM IONS, CORRESPONDING MAGNESIUM COMPLEXES, AND TEST DEVICES AND ION SELECTIVE PARTS CONTAINING SUCH HEXACARBOXYLIC ACID HEXA-AMIDES

[75] Inventors: Wilhelm Simon; Marizel V. Rouilly, both of Zürich; Bruno Rusterholz, Thalwil, all of Switzerland

[73] Assignee: Willi Moller AG, Zurich, Switzerland

[21] Appl. No.: 963,922

[22] Filed: Oct. 20, 1992

Related U.S. Application Data

[63] Continuation of Ser. No. 488,560, Mar. 2, 1990, abandoned.

[30] Foreign Application Priority Data

Mar. 3, 1989 [CH] Switzerland ............................ 811/89

[51] Int. Cl.$^5$ ............................................. C07C 233/06
[52] U.S. Cl. .................................... 564/153; 564/152; 564/156
[58] Field of Search .................. 564/153, 152, 156; 528/288, 292

[56] References Cited

U.S. PATENT DOCUMENTS

| | | | |
|---|---|---|---|
| 2,130,523 | 9/1938 | Carothers et al. | 564/153 |
| 2,130,948 | 9/1938 | Carothers et al. | 564/153 |
| 2,163,584 | 6/1939 | Carothers et al. | 564/153 |
| 3,957,607 | 5/1976 | Simon et al. | 204/180 P |
| 4,785,111 | 11/1988 | Toda | 564/153 |
| 4,830,671 | 5/1989 | Frihart et al. | 106/27 |

FOREIGN PATENT DOCUMENTS

| | | | |
|---|---|---|---|
| 1271476 | of 1976 | Australia . | |
| 264755 | 4/1988 | European Pat. Off. . | |
| 1092233 | 4/1989 | Japan | 564/153 |

OTHER PUBLICATIONS

Lanter et al. "Neutral Carrier Based Ion Selectivity Electrode or Intracellular Magnesium Activity Study", Analytical Chemistry, vol. 52, No. 14, 2400–2402 (Dec. 1980).

Erne et al., "Lipophilic Di- and Triamides as Ionophores for Alkaline Earthmetal Cations", Helvetia Chimica Acta, vol. 63, Fasc. 8, 2271–2279 (1980).

Erne et al., "Lipophilic Diamides as Ionophores for Alkali and Alkaline Earthmetal Cations", Helvetia Chimica Acta, vol. 65, Fasc. 2, 538–545 (1982).

Rouilly et al., "Neutral-Carrier-Based Magnesium-Selective Electrode", Analytical Chemistry, vol. 60, No. 19, 2013–2106 (Oct. 1988).

Muller et al., "Magnesium-Selective Electrodes for Blood Serum Studies and Water Hardness Measurement", Mikrochem. Acta [Vienna], vol. 3, 283–290 1988.

Primary Examiner—Richard L. Raymond
Assistant Examiner—Shailendra Kumar
Attorney, Agent, or Firm—Seidel, Gonda, Lavorgna & Monaco

[57] ABSTRACT

Hexacarboxylic acid hexa-amides are described which form new lipophilic magnesium complexes with magnesium ions. The hexa-amides are preferably novel compounds comprising three dicarboxylic acid diamide moieties interconnected to form a non-cyclic, monocyclic, bicyclic, tricyclic or polycyclic structure. Test devices such as test trips or ion-selective members are provided which contain hexacarboxylic acid hexa-amides as the ion-selective component. The test devices have a high selectivity for magnesium ions over alkali metal ions and other alkaline earth metal ions. Selectivity for magnesium ions over sodium and calcium ions permits determination of magnesium concentration in biological materials, including body fluids such as blood serum or whole blood. Magnesium concentration and activity can also be determined in sample solutions having a neutral or slightly acidic pH.

8 Claims, 1 Drawing Sheet

HEXACARBOXYLIC ACID HEXA-AMIDES WHICH FORM LIPHOPHILIC COMPLEXES WITH MAGNESIUM IONS, CORRESPONDING MAGNESIUM COMPLEXES, AND TEST DEVICES AND ION SELECTIVE PARTS CONTAINING SUCH HEXACARBOXYLIC ACID HEXA-AMIDES

This is a continuation of co-pending application Ser. No. 07/488,560 filed on Mar. 2, 1990, now abandoned.

BACKGROUND OF THE INVENTION

There are described in the prior art carboxylic acid amides, namely dicarboxylic acid diamides, and some tricarboxylic acid triamides and tetracarboxylic acid tetraamides, which have the ability of forming lipophilic complexes with several kinds of cations. It is furthermore also known that these carboxylic acid amides may be used as ion-sensitive components in ion-sensitive parts for the determination of cations in sample solutions.

For a long time, investigations were made to develop carboxylic acid amides which are sufficiently selective for magnesium ions over alkali metal ions and calcium ions, to permit the determination of magnesium ions in sample solutions containing sodium ions, calcium ions and potassium ions. The known lipophilic complex-forming agents for magnesium had at best only about the same selectivity for magnesium ions as for calcium ions; or the determination of magnesium ions was possible only in sample solutions having a basic pH. Higher concentrations of protons interfered with magnesium ion determination.

It is the object of the present invention to provide carboxylic acid amides which have a sufficiently high selectivity for magnesium ions over other alkali metal ions and alkaline earth metal ions so that the determination of magnesium ions may be performed in sample solutions of biological origin, e.g., body fluids. It is a further object to provide carboxylic acid amides which also have the ability to form lipophilic complexes with magnesium ions in the presence of higher activities of $H_3O+$ ions. This permits determination of magnesium ions in sample solutions which have a neutral pH or even slightly acidic pH, e.g., a pH value in the range of 5.5 to 7.5.

DESCRIPTION OF THE PRIOR ART

More than 15 years ago, dicarboxylic acid diamides were prepared which had the ability to form lipophilic complexes with cations, for example, metal cations. Such dicarboxylic acid diamides are described in U.S. Pat. No. 3,957,607 of Simon et al.

F. Lanter, D. Erne, D. Ammann and W. Simon, *Analytical Chemistry*, vol. 52, no. 14, Dec. 1980, pages 2400–2402, describe magnesium-selective microelectrodes in which the magnesium-selective component is a succinic acid diamide, and the amide-forming amine is n-heptyl-methyl-amine. These magnesium-selective microelectrodes, however, can be only used for intra-cellular measurements of magnesium ion activities, and not for the determination of magnesium ions in biological material. The intracellular sodium concentration is far lower than the sodium concentration in biological material, such as body fluids. The selectivity of the disclosed succinic acid diamides for magnesium ions over sodium ions is insufficient to enable determination of magnesium ions in sample solutions containing far higher concentrations of sodium ions than magnesium ions. This is true for body fluids. Furthermore, the selectivity of the succinic acid diamides for magnesium ions over calcium ions is not high enough.

D. Erne, N. Stojanac, D. Ammann, P. Hofstetter, E. Pretsch and W. Simon, *Helvetica Chimica Acta*, vol. 63, number 8, pages 2271–1179, 1980, explain that the octahedral coordination sphere seems to be preferred in magnesium complexes. Dicarboxylic acid diamides, and several tricarboxylic acid triamides, were investigated, because it was assumed that tricarboxylic acid triamides have the ability of forming 1:2 cation/ligand complexes, i.e. complexes in which two molecules of the tricarboxylic acid triamide are arranged around the $Mg^{2+}$ central ion. The six oxygen atoms of the two tricarboxylic acid triamide form, together with the magnesium ion, a complex having an octahedral structure.

The tricarboxylic acid triamides which were investigated by Erne et al., supra, correspond to the following structural formula A

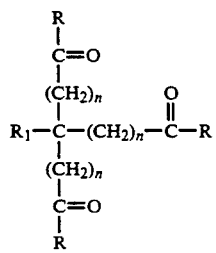

in which $R_1$ is a hydrogen atom or a methyl group, n is 0 or the integer 1 or 2, and the amide-forming amine R is either a secondary dialkylamine having 4 or 6 carbon atoms in each of the two alkyl groups, methyl-n-heptylamine or dicyclohexyl amine.

Erne et al. compared the magnesium selectivity of the formula A tricarboxylic acid triamides with dicarboxylic acid diamides in which the amide-forming amine was identical with the amide-forming amine of the corresponding compounds of formula A. That is, the corresponding diamides of oxalic acid, malonic acid and succinic acid were tested. Furthermore, tests were also performed with the dicyclohexyl amine of glutaric acid. Diamides formed from succinic acid and n-heptyl-methyl amine preferred calcium ions over magnesium ions by a factor of about 20. Quite unexpectedly, however, the triamide of formula A in which $R_1$ was hydrogen, two of n were 1, and one of n was 0, and in which the amide-forming amine was n-heptyl-methyl amine, had a worse selectivity for magnesium ions over calcium ions than the corresponding succinic acid diamide. None of the other tricarboxylic acid triamides of formula A tested had a selectivity for magnesium ions over calcium ions, or for magnesium ions over alkali metal ions. Quite surprisingly, the tricarboxylic acid triamides of formula A in which the radical $R_1$ was hydrogen, all n were 0, and the amide-forming amine was dicyclohexyl amine, had some selectivity for cesium ions ($Cs+$) over other alkali metal ions, as well as over alkaline earth metal ions.

D. Erne, N. Stojanac, D. Ammann, E. Pretsch and W. Simon, *Helvetica Chimica Acta*, vol. 63, number 8, pages 2264–2270, 1980, tested further dicarboxylic acid diamides and tricarboxylic acid triamides for magnesium ion-selectivity. One tetracarboxylic acid tetraamide was tested as well. The tested tricarboxylic acid triamides differed structurally from the tricarboxylic acid triamides of formula A in that the central atom was a nitrogen atom, not a carbon atom as in the compounds of formula A. Furthermore, n was 1 in the tested triamides. The tested dicarboxylic acid diamides comprised compounds in which a nitrogen atom was present in the group to which the two carboxylic acid amides were bonded (i.e. a tertiary amino group). Alternatively, the amide-bonding groups contained the oxygen atom of an ether group or the sulphur atom of a corresponding thioether group. It was assumed that the electron pairs of these heteroatoms (N, O and S) would form, together with the oxygen atoms of the two carboxylic acid amides, complexes with magnesium ions. Thus it was expected that these dicarboxylic acid diamides would form 1:2 cation/ligand complexes.

The tetracarboxylic acid tetraamide which was tested by Erne al., *Helvetica Chimica Acta*, 63 (8), 2264–2270, 1980, had the following structural formula B

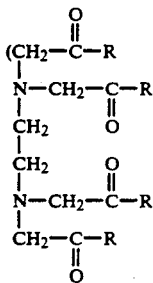

in which the amide-forming amine was n-heptyl-methyl amine. It was assumed that the electron pairs on the two nitrogen atoms and four oxygen atoms of the tetracarboxylic acid tetraamides could constitute binding sites for the formation of corresponding complexes having a magnesium ion as the central ion. Because of the six possible binding sites, the formation of a 1:1 cation/ligand complex having an octahedro structure was expected. Contrary to this, however, none of the dicarboxylic acid diamides, tricarboxylic acid triamides and tetracarboxylic acid tetraamides which were tested according to Erne et al. for magnesium ion selectivity had a revelent selectivity in plastic material membranes for magnesium ions over calcium ions, or for magnesium ions over alkali metal ions. In particular, there was no revelent selectivity for magnesium ions over sodium ions. Quite surprisingly, the tetracarboxylic acid tetraamides of formula B even had a higher selectivity for barium ions, calcium ions and sodium ions than for magnesium ions. The tetracarboxylic acid tetraamide was therefore completely unsuited for the intended purpose.

D. Erne, D. Ammann, A. F. Zhukov, F. Behm, E. Pretsch and W. Simon in *Helvetica Chimica Acta.* vol. 65, number 2, pages 538–545, 1982, describe a large number of dicarboxylic acid diamides all of which were tested in ion-selective membranes for their selectivity for different kinds of alkali metal ions and alkaline earth metal ions. However, none of the tested dicarboxylic acid diamides had a higher selectivity for magnesium ions than for alkali metal ions or other alkaline earth metal ions. In spite of the intensive research work performed in these fields of application, until very recently the specific succinic acid diamide in which n-heptyl-methyl amine was the amide-forming amine was the one compound assumed to be possibly modifiable in structure to result in a suitable lipophilic complex-forming agent for magnesium ions.

M. V. Rouilly, M. Badertscher, E. Pretsch, G. Suter and W. Simon, *Analytical Chemistry*, vol. 60, number 19, pages 2013–2106, October, 1989, describe a magnesium-selective electrode in which the magnesium-selective component is the specific derivative of the above-stated succinic acid diamide, in which an amino substituent is bonded to one of the two carbon atoms of the carboxylic acid moiety, i.e. one of the two carbon atoms of the chain having the structure —$CH_2$—$CH_2$—. This amino-substituted dicarboxylic acid diamide, is the amide of aspartic acid in which the amide-forming amine is n-heptyl-methyl amine. It actually had a rather good selectivity for magnesium ions over other alkali metal ions and alkaline earth metal ions, including calcium ions. This was true if the diamide was employed as the ion-selective component of an ion-selective membrane wherein the polymeric component was polyvinylchloride and the plasticizer was o-nitrophenyloctylether, and wherein the membrane furthermore contained an ion exchanger. The latter was the potassium salt of tetraphenylborate wherein the phenyl nuclei of the tetraphenylborate radical were all monochloro-substituted in the para-position. The resulting ion selectivity is illustrated in FIG. 3 of Rouilly et al.

A severe disadvantage of the Rouilly et al. magnesium-selective component is that a determination of magnesium ions is only possible in sample solutions having a pH value in the basic range, i.e., in the range of 8–9. If the pH value of the sample solution is below 8, the higher concentration of $H_3O^+$ ions interferes with magnesium ion complex formation. Protons react with the free amino group of the stated amino-substituted dicarboxylic acid diamide.

In most recent times, magnesium-selective electrodes were prepared for the determination of magnesium ions in blood serum, and for the measurement of water hardness. The ion-sensitive part of these electrodes contained a tetracarboxylic acid tetraamide as the magnesium-selective component. The electrodes are described in detail in the publication of M. Muller, M. Rouilly, B. Rusterholz, M. Maj-Zurawska, Z. Hu and W. Simon in *Mikrochim. Acta* [Vienna], III, pages 283–290, 1988. The tetracarboxylic acid tetraamides tested in the magnesium-selective electrodes corresponded to the following formula C

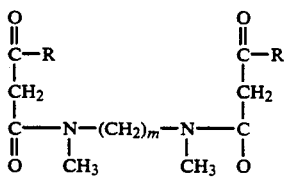

The radical R is the amide-forming amine moiety. The amine in the tested compounds was n-heptyl-methyl amine; m was the integer 4, 6, 8, or 10. The m=8 compound had the best properties, provided it was used as the ion selective-component in an ion-selective membrane in which: the polymeric component was polyvinylchloride; the plasticizer was selected from chloroparaffin, an o-nitrophenylether, or a mixture thereof; and the ion exchanger was the above-stated potassium salt of the para-chloro-substituted tetraphenylborate. Nevertheless, the best of the magnesium selective membranes tested by Muller et al. had about the same selectivity for calcium ions and for magnesium ions (see FIG. 4 of Muller et al.).

French patent publication 2,306,683 of Bayer describes several carboxylic acid amides. Formula I of claim 1 on page 101 also comprises hexacarboxylic acid hexaamides, provided n is 4. However, in the complete specification, not even a single hexacarboxylic acid hexaamide is specifically mentioned. Furthermore, the corresponding carboxylic acid amides are used as active ingredients in pharmaceutical preparations for treating hypolipidaemia. Nothing is stated in French patent publication 2,306,683 that the corresponding carboxylic acid amides have the ability of forming lipophilic complexes with any cation.

SUMMARY OF THE INVENTION

The object of the present invention is to provide carboxylic acid amides which have the ability of forming lipophilic complexes with magnesium ions. By using these carboxylic acid amides as ion-selective components, it furthermore should be possible to provide ion-sensitive parts which have a high selectivity for magnesium ions over other alkaline earth metal ions, particularly calcium ions, and a high selectivity for magnesium ions over alkali metal ions. It furthermore should be possible to provide ion-sensitive parts with which magnesium ions can be determined in sample solutions which have a neutral pH, or even an acidic pH.

Quite unexpectedly it was found that the intended aims can be achieved with hexacarboxylic acid hexaamides.

DESCRIPTION OF THE INVENTION

Figure 1:
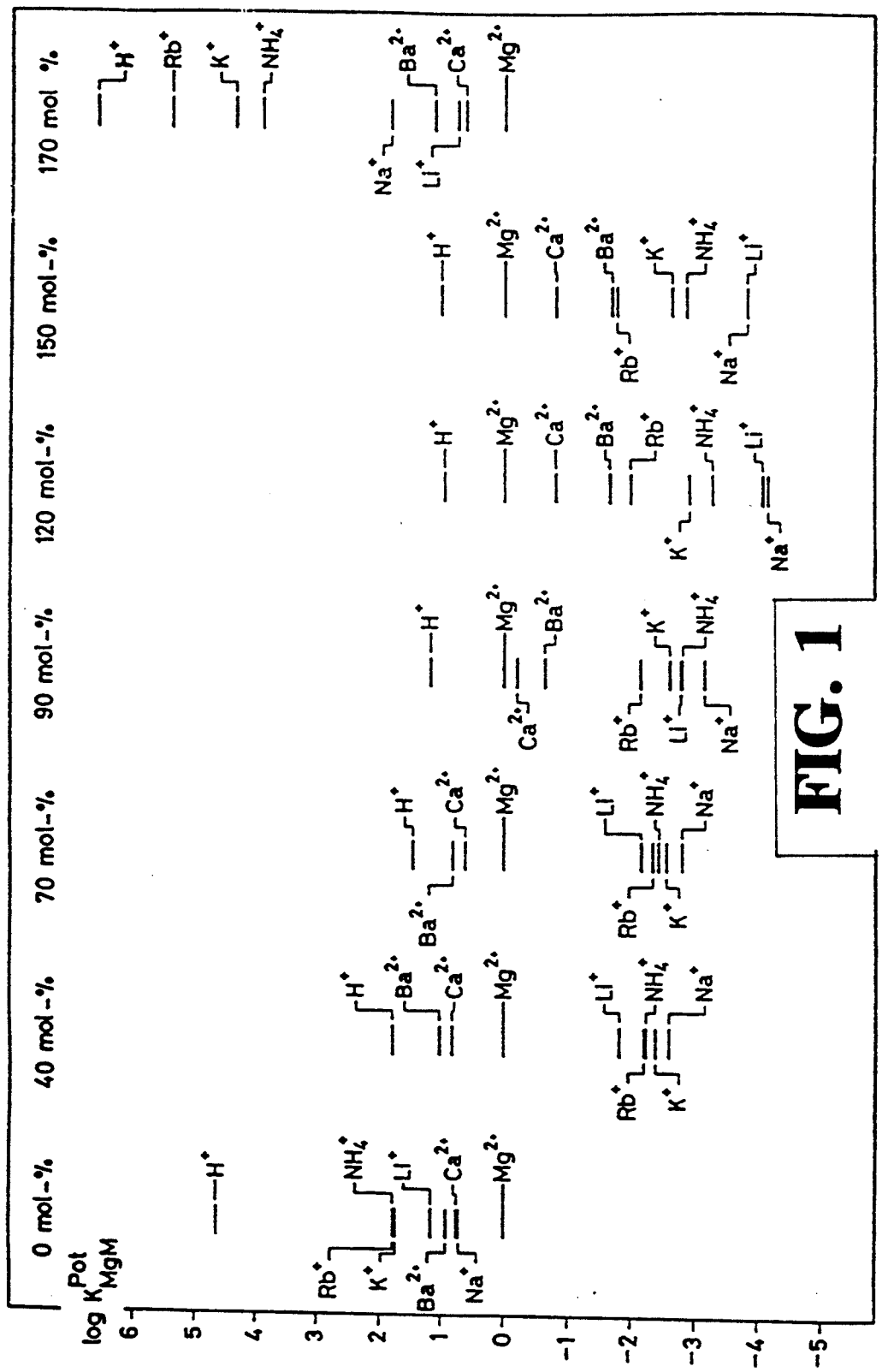
FIG. 1 illustrates the selectivity factors for $10^{-1}$ molar aqueous solutions of metal and ammonium chlorides of ion selective membranes according to the invention, which membranes have from 0 mol-% to 170 mol-% of the tetrakis-(p-chlorophenyl)borate potassium salt per 100 mol-% of the hexacarboxylic acid hexa-amide of Formula IIIa.

One objection of the present invention is to provide a carboxylic acid amide which forms complexes with magnesium ions wherein the carboxylic acid amide is a hexacarboxylic acid hexa-amide which forms lipophilic complexes with magnesium ions. The present invention furthermore also concerns the corresponding lipophilic complexes of these hexacarboxylic acid hexa-amides with magnesium ions.

Preferred inventive carboxylic acid amides are the corresponding hexacarboxylic acid hexa-amide in which, per molecule of the hexacarboxylic acid hexaamide, there are present three dicarboxylic acid diamide groups having the following formulae I, I' and I":

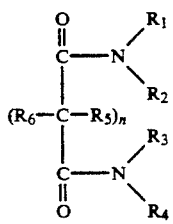

I

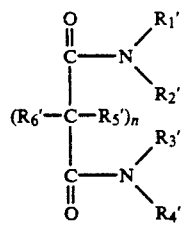

I'

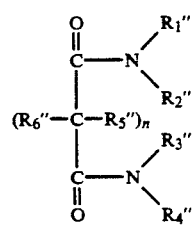

I"

wherein the radicals $R_1$, $R_2$, $R_3$, $R_1'$, $R_1'$, $R_3'$, $R_4'$, $R_1''$, $R_2''$, $R_3''$ and $R_4''$ have independently from each other the meaning of hydrogen atoms, unsubstituted alkyl radicals, substituted alkyl radicals, unsubstituted alkenyl radicals, substituted alkenyl radicals, unsubstituted alkynyl radicals, substituted alkynyl radicals, unsubstituted cycloalkyl radicals, substituted cycloalkyl radicals, unsubstituted aromatic radicals, substituted aromatic radicals, unsubstituted heterocyclic radicals or substituted heterocyclic radicals or combinations of the stated radicals; or the radical $R_1$ forms together with the radical $R_2$ and the nitrogen atom to which said radicals are bonded and/or the radical $R_1'$ forms together with the radical $R_2'$ and the nitrogen atom to which said radicals are bonded, or the radical $R_1''$ forms together with the radical $R_2''$ and the nitrogen atom to which said radicals are bonded, a heterocyclic ring which optionally comprises further hetero atoms; and/or the radical $R_3$ and the radical $R_4$ form together with the nitrogen atom to which said radicals are bonded, and/or the radical $R_3'$ and the radical $R_4'$ form together with the nitrogen atom to which said radicals are bonded, and/or the radical $R_3''$ and the radical $R_4''$ forms together with the nitrogen atom to which said radicals are bonded, a heterocyclic nucleus which optionally comprises further hetero atoms;

or the radical $R_1$ or the radical $R_2$ bonded to one of the two nitrogen atoms of the dicarboxylic acid diamide moiety of formula I forms together with the radical $R_3$ or $R_4$ which is bonded to the other of the two nitrogen atoms of the dicarboxylic acid diamide structure of formula I, a group which cyclizes the dicarboxylic diamide group of formula I, forming a corresponding heterocyclic structure; and/or the radical $R_1'$ or the radical $R_2'$ bonded to one of the nitrogen atoms of the dicarboxylic acid diamide moiety of formula I' forms together with the radical $R_3'$ or $R_4'$ which is bonded to the other of said nitrogen atoms of the dicarboxylic diamide group of formula I', a divalent group which cyclizes the dicarboxylic acid diamide structure of formula I',
forming a corresponding cyclic structure; and/or the radical $R_1''$ or the radical $R_2''$ bonded to one of the nitrogen atoms of the dicarboxylic acid diamide structure of formula I'' forms together with the radical $R_3''$ or the radical $R_4''$, which is bonded to the other nitrogen atom of the dicarboxylic acid diamide moiety of formula I'', a divalent group which cyclizes the dicarboxylic acid diamide group of formula I'', forming a corresponding cyclic structure;

$R_5$, $R_6$, $R_5'$, $R_6'$, $R_5''$ and $R_6''$ are, independently from each other, hydrogen atoms, alkyl radicals having 1-4 carbon atoms or halo atoms;

n, n' and n'' are, independently from each other, 0 or an integer in the range of 1-3;

wherein however at least one of the radicals $R_1$, $R_2$, $R_3$, $R_4$, $R_5$ and $R_6$ of the dicarboxylic acid moiety of formula I forms together with a corresponding radical $R_1'$, $R_2'$, $R_3'$, $R_4'$, $R_5'$, $R_6'$, $R_1''$, $R_2''$, $R_3''$, $R_4''$ $R_5''$ or $R_6''$ of the other two dicarboxylic acid diamide structures of formulae I' and I'', respectively, a divalent aliphatic, alicyclic, aromatic or heteroaromatic group or a combination of such radicals, through which divalent group the dicarboxylic acid diamide group of formula I is bonded through a nitrogen atom thereof, or through a carbon atom thereof, to a nitrogen atom or a carbon atom of the dicarboxylic acid diamide moiety having the formula I', or the dicarboxylic acid diamide moiety having the formula I'';

so that there is formed the corresponding hexacarboxylic acid hexa-amide which comprises the dicarboxylic acid moiety of formula I, the dicarboxylic acid moiety of formula I', as well as the dicarboxylic acid moiety of formula I''; and wherein the total structure of said hexacarboxylic acid hexa-amide is not a cyclic, monocyclic or polycyclic structure.

Preferred inventive magnesium complexes are those formed between magnesium and the preferred hexacarboxylic acid hexa-amides which have in their structure dicarboxylic acid diamide moieties corresponding to the above-stated formulae I, I' and I''. It was found that these new magnesium complexes are 1:1 complexes formed from one $Mg^{2+}$ cation and one molecule of hexacarboxylic acid hexa-amide.

One preferred class of hexacarboxylic acid hexa-amides which contain three dicarboxylic acid diamide moieties corresponding to the formula I, I' and I'' are the hexacarboxylic acid hexa-amides of the following formula II

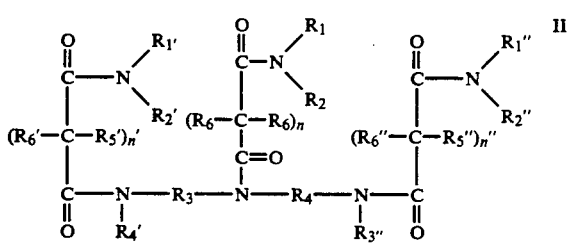

wherein
the radicals $R_3$ and $R_4$ are independently from each other divalent aliphatic, alicyclic, aromatic or heteroaromatic radicals, or a combination of such radicals;

the radicals $R_1$, $R_2$, $R_1'$, $R_2'$, $R_1''$, $R_2''$, $R_4'$ and $R_3''$ have the same meaning as defined above with regard to the corresponding dicarboxylic acid moieties of formulae I, I' and I'' respectively; or the radical $R_1'$ forms together with the radical $R_2$ and/or the radical $R_1'''$ forms together with the radical $R_2'$ and/or the radical $R_1'''$ forms together with the radical $R_2'$ and the corresponding nitrogen atom to which said radicals are bonded, a heterocyclic ring;

$R_5$, $R_6$, $R_5'$, $R_6'$, $R_5''$, and $R_6''$ have the same meaning as defined above with regard to the corresponding radicals of the dicarboxylic acid diamide moieties of formulae I, I' and I'' respectively;

or the radical $R_2$ and/or the radical $R_1$ form together with the radical $R_1'$, $R_2'$, $R_4'$, $R_3''$, $R_2''$ or $R_1''$ a divalent radical; and/or the radical $R_1'$ and/or the radical $R_2'$ forms together with the radical $R_3''$ or $R_2''$ or $R_1''$ a divalent radical; and/or the radical $R_1''$ or the radical $R_2''$ forms together with the radical $R_4'$ a divalent radical; and wherein said divalent radicals are aliphatic, alicyclic, aromatic or heteroaromatic radicals or a combination of two such radicals through which the hexacarboxylic acid hexa-amides of formula II are ringclosed, forming a corresponding hexacarboxylic acid hexa-amide which as a monocyclic, bicyclic, tricyclic or polycyclic structure.

A further group of preferred hexacarboxylic acid hexa-amides which selectively form lipophilic complexes with magnesium ions and which have in their structure three dicarboxylic acid diamide moieties corresponding to formula I, I' and I'', respectively, are the hexacarboxylic acid hexa-amides which correspond to the following formula VIII

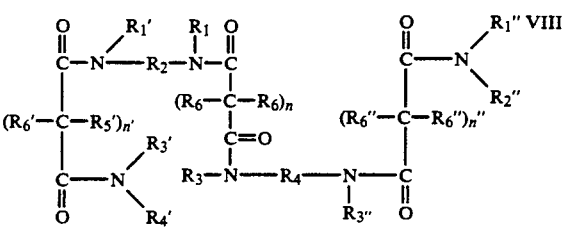

wherein
the radicals $R_2$ and $R_4$ are independently from each other divalent aliphatic, alicyclic, aromatic or heteroaromatic radicals or a combination of such radicals; and the radicals $R_1$, $R_1'$, $R_1''$, $R_2''$, $R_3$, $R_3'$, $R_4'$ and $R_3''$, have the same meaning as defined above with regard to the corresponding dicarboxylic acid moieties of formulae I, I' and I'' respectively; or the radical $R_1''$ forms together with the radical $R_2''$ and/or the radical $R_3'$ forms together with the radical $R_4'$ and/or the radical $R_1$ forms together with the radical $R_3$ and the corresponding nitrogen atom to which said radicals are bonded, a heterocyclic ring;.

$R_5$, $R_6$, $R_5'$, $R_6'$, $R_5''$ and $R_6''$ have the same meaning as defined above with regard to the corresponding radicals of the dicarboxylic acid diamide moieties of formulae I, I' and I'' respectively; or the radical $R_3$ and/or the radical $R_1$ forms together with the radical $R_1'$, $R_3'$, $R_4'$, $R_3''$, $R_2''$ or $R_1''$ a divalent radical; and/or the radical $R_3'$ and/or the radical $R_4'$ forms together with the radical $R_3''$ or $R_2''$ or $R_2''$ a divalent radical; and/or the radical $R_1''$ or the radical $R_2''$ forms together with the radical $R_4'$ a divalent radical; and wherein the said divalent radicals are aliphatic, alicyclic, aromatic or heteroaromatic radicals or a combination of two such radicals, through which the hexacarboxylic acid hexa-amides of formula VIII are ringclosed, forming a corresponding hexacarboxylic acid hexa-amide which has a monocyclic, bicyclic, tricyclic or polycyclic structure.

In preferred inventive hexacarboxylic acid hexa-amides, in the three dicarboxylic acid diamide moieties corresponding to the formulae I, I' and I'', as well as in the preferred hexacarboxylic acid hexa-amide having the formula II and VIII, respectively, the symbols n, n' and n'' have, independently from each other, the meaning of the integer 1 or the integer 2. In corresponding hexacarboxylic acid hexa-amides in which n, n' and n'' are 1 or 2, the distance between the two oxygen atoms of the dicarboxylic acid diamides seems to be ideal to enable an interaction of the six oxygen atoms of the three dicarboxylic acid moieties with the magnesium ion, in order to form a complex with the magnesium ion as the central atom. The complex has an octahedral structure.

Nevertheless, however, such hexacarboxylic acid hexa-amides are able to form stable magnesium complexes in which one, two or all of the symbols n, n' and n'' are 0 or the integer 3. However, as outline above, the corresponding compounds in which all or most of the symbols n, n' and n'' are 1 or 2, seem to result in even more stable magnesium complexes.

It was found from tests that hexacarboxylic acid hexa-amides having the three dicarboxylic acid diamide structures of formulae I, I' and I'', and in which n, n' and n'' are 4, 5 or higher, no longer have the ability to form high stability complexes with magnesium ions. Therefore, in as far as the particularly preferred hexacarboxylic acid hexa-amides of formulae II and VIII are concerned, the symbols n, n' and n'' were defined so that their values must not be higher than 3.

In the inventive hexacarboxylic acid hexa-amides comprising the three dicarboxylic acid moieties having the structures I, I' and I'', the substituents $R_5$, $R_6$, $R_5'$, $R_6'$, $R_5''$ and $R_6''$ must not be too voluminous. Voluminous substituents would sterically hinder the approach of the magnesium ion to the two carbonyl groups of each of the three dicarboxylic acid diamide moieties of formulae I, I' and I''. Because of this, in the dicarboxylic acid diamide moieties of formulae I, I' and I'', as well as in the preferred hexacarboxylic acid hexa-amides of formulae II and VIII, the aforementioned radicals are hydrogen, alkyl having 1–4 carbon atoms, or halogen. In order that steric hindrance is prevented, small alkyl groups, such as methyl, and small halogen atoms such as chlorine or fluorine, are preferred. In the preferred hexacarboxylic acid hexa-amides, accordingly, all the radicals $R_5$, $R_6$, $R_5'$, $R_6'$, $R_5''$ and $R_6''$ are either hydrogen or methyl. Particularly preferred are those hexacarboxylic acid hexa-amides in which all of the aforesaid are hydrogen atoms.

If in the preferred inventive hexacarboxylic acid hexa-amides, which comprise in their structure dicarboxylic acid diamide moieties corresponding to formulae I, I' and I'', n is 1 or 2 and, furthermore, if all of the substituents $R_5$, $R_6$, $R_5'$, $R_6'$, $R_5''$ and $R_6''$ are hydrogen, then the corresponding dicarboxylic acid diamide moieties are such moieties which are derived from malonic acid diamide and succinic acid diamide. Tests have shown that particularly stable magnesium complexes are formed if in the hexacarboxylic acid hexa-amides at lest one, preferably two, and still more preferred, all three of the dicarboxylic acid diamide structures of formulae I, I' and I'', are derived from malonic acid, and the remaining dicarboxylic acid diamide moieties are derived from succinic acid diamides.

A further object of the present invention is to provide a process for preparing new lipophilic complexes of magnesium ions and hexacarboxylic acid hexa-amides, which process is characterized in that magnesium ions are brought into contact with the hexacarboxylic acid hexa-amides.

Lipophilic magnesium complexes with hexacarboxylic acid hexa-amides are not known from the prior art, and therefore all such inventive magnesium complexes are new compounds.

Also, the hexacarboxylic acid hexa-amides which have in their structures three dicarboxylic acid diamide moieties of formulae I, I' and I'', are new chemical compounds. Therefore the corresponding complex-forming hexacarboxylic acid hexa-amides, as well as the magnesium complex of said compounds, are new compounds.

The preferred inventive hexacarboxylic acid hexa-amides are those formed with magnesium ions and the preferred hexacarboxylic acid hexa-amides having the structures II and VIII, respectively. Particularly preferred are compounds in which the substituents have the preferred meaning outlined above for the corresponding compounds of formula II and VIII, respectively.

As outlined above, magnesium ions have the tendency to form complexes in which the central ion, i.e. the magnesium ion, is surrounded by six heteroatoms. Due to the interaction of the magnesium ion with the six heteroatoms, a complex having an octrahedral structure is formed. Accordingly, the preferred inventive complexes of magnesium and hexacarboxylic acid hexa-amides are 1:1 cation/ligand-complexes. Such complexes are formed from one mol of magnesium cations and one mol of hexacarboxylic acid hexa-amides.

As already outlined above, the inventive magnesium complexes of the hexacarboxylic acid hexa-amides must have lipophilic properties. Therefore, the corresponding complex forming agent, i.e. the hexacarboxylic acid hexa-amide, is preferably free of any substituents which have strong hydrophilic properties, such as carboxylic acid groups and sulphonic acid groups. The hexacarboxylic acid hexa-amides should preferably contain only a few hydroxy groups per molecule, most preferably no hydroxy groups per molecule.

In the preferred hexacarboxylic acid hexa-amides of formula II and VIII, the radicals $R_3$ and $R_4$ in the case of the hexacarboxylic acid hexa-amides of formula II, and the radicals $R_2$ and $R_4$ in the case of the hexacarboxylic acid hexa-amides of formula VIII, are independently from each other, divalent aliphatic, alicyclic, aromatic or heteroaromatic radicals which bind the three dicarboxylic acid diamide moieties to each other, forming the corresponding hexacarboxylic acid hexa-amides. Optionally, however, in the hexacarboxylic acid hexa-amides of formula II and VIII, there are present further such divalent aliphatic, alicyclic, aromatic or heteroaromatic radicals or combinations thereof through which the hexacarboxylic acid hexa-amides of formula II and VIII are ringclosed, forming corresponding hexacarboxylic acid hexa-amides of formula II and VIII, which have a monocyclic, bicyclic, tricyclic, tetracyclic or polycyclic structure.

Preferred divalent groups which bind the three dicarboxylic acid amide structures of formulae I, I' and I'' together, forming the corresponding hexacarboxylic acid amides, (i.e. the groups $R_3$ and $R_4$ of the hexacarboxylic acid hexa-amides of formula II, and the groups $R_2$ and $R_4$ of the hexacarboxylic acid hexa-amide of formula VIII) are aliphatic groups which have a carbon main chain. The divalent radicals which perform the ring closing to form corresponding hexacarboxylic acid hexa-amides of formula II and VIII are also preferably aliphatic groups which have a carbon main chain. The carbon main chain can be derived from a saturated aliphatic chain. One or two carbon-carbon double bonds can be optionally present in the aliphatic main chain. Furthermore, the corresponding main chain of the divalent residues can be interrupted through heteroatoms, e.g., one or several ether oxygen atoms, thioether oxygen atoms or groups having the formula

in which $R^-$ is hydrogen or an aliphatic, alicyclic, aromatic or heteroaromatic residue. Preferably $R^-$ is hydrogen or an alkyl group having 1–4 carbon atoms.

In order to provide the inventive hexacarboxylic acid hexa-amides and the magnesium complexes formed therefrom with the necessary lipophilic properties, it is furthermore advantageous if the hexacarboxylic acid hexa-amides contain at least one optionally substituted alkyl radical, alkenyl radical or alkynyl radical comprising at least four carbon atoms. It is further advantageous that the two nitrogen atoms of two different dicarboxylic acid diamide moieties of formulae I, I' and I'', or one nitrogen atom and one carbon atom of two different dicarboxylic acid diamide groups of formulae I, I' and I'', or two carbon atoms of two different dicarboxylic acid moieties of formulae I, I' and I'', are bonded to each other through an optionally substituted divalent aliphatic group of at least four carbon atoms which may contain one or two C—C double bonds or C—C triple bonds. Preferably, the number of carbon atoms in at least one of the optionally substituted alkyl, alkenyl or alkynyl radicals is 5–15. Particularly preferred are radicals having 6–12 carbon atoms. The above-stated divalent aliphatic groups through which two nitrogen atoms, one nitrogen atom and one carbon atom, or two carbon atoms of two different dicarboxylic acid diamide structures of formulae I, I' and I'', are connected with each other, are divalent aliphatic groups comprising a chain of at least four carbon atoms. Particularly preferred are such compounds of formula II in which the radical $R_3$, and also the radical $R_4$, is a divalent aliphatic group comprising at least four carbon atoms, preferably a corresponding alkylene group. Particularly preferred is a straight chain alkylene radical having the formula

in which n is an integer in the range of 4–15, preferably 5–15, most preferably, 6–12.

The same is also true for the radicals $R_2$ and $R_4$ of the preferred hexacarboxylic acid hexa-amides having the structure VIII. Said radicals as well are preferably straight chain alkylene radicals having the above-stated structure wherein n has the meaning stated above.

If the above-defined preferred hexacarboxylic acid hexa-amides of formula II are non-cyclic compounds, then the radicals $R_1$, $R_1'$ and $R_1''$ are preferably alkyl groups having 4–15 carbon atoms, more preferably 5–14 carbon atoms, and most preferably 6–12 carbon atoms, or cycloalkyl groups. The preferred cycloalkyl group is cyclohexyl. Of the stated alkyl groups those which are preferred have in their structure not more than three branchings, preferably not more than two branchings. Particularly preferred are straight chain alkyl groups.

The above considerations are also true for the corresponding substituents $R_3'$ and $R_1''$ of the particularly preferred hexacarboxylic acid hexa-amides of formula VIII.

Preferred hexacarboxylic acid hexa-amides of formula II have a non-cyclic structure and the radical $R_2$, $R_2'$ and $R_2''$ are preferably hydrogen atoms, optionally substituted alkyl groups having 1–15 carbon atoms, cycloalkyl groups or optionally substituted aromatic nuclei, e.g. phenyl nuclei. Preferred are the following: hydrogen; unsubstituted alkyl radicals, i.e., those having a short chain, such as methyl; long chain radicals such as the above-stated long chain radicals; and cyclohexyl.

In as far as non-cyclic hexacarboxylic acid hexaamides of formula VIII are concerned, the same considerations are also true for the corresponding radicals $R_4'$, $R_2''$, $R_1'$, $R_1$, $R_3$, and $R_3''$.

Provided that the corresponding hexacarboxylic acid hexa-amides of formula II have a monocyclic, bicyclic, tricyclic or polycyclic structure, then $R_1$ forms together with the radical $R_1'$, or together with the radical $R_1''$, an alkylene group having the structure

in which z is an integer in the range of 4–15, so that the corresponding hexacarboxylic acid hexa-amides have a monocyclic structure; or in the hexacarboxylic acid hexa-amides of formula II, the radical $R_1$ forms together with the radical $R_1'$, and the radical $R_2$ forms together with the radical $R_1''$, alkylene groups having the structure

in which z is an integer in the range of 4–15, which hexacarboxylic acid hexa-amides of formula II accordingly have a tricyclic structure; or in the hexacarboxylic acid hexa-amides, the radical $R_1'$ forms together with the radical $R_1''$ an alkylene group having the structure

wherein z is an integer of 4–15, which hexacarboxylic acid hexa-amides accordingly have a cyclic structure.

Preferably in the above-stated groups z is an integer in the range of 5-14, most preferably, in the range of 6-12.

The same considerations are true if in the preferred hexacarboxylic acid hexa-amides of formula VIII, the radical $R_3'$ forms together with the radical $R_1''$, or together with the radical $R_3$, an alkylene group having the structure $$-(CH_2)_z-,$$

so that the corresponding hexacarboxylic acid hexa-amides of formula VIII have a monocyclic structure; or, if in the hexacarboxylic acid hexa-amides of formula VIII, the radical $R_3'$ forms together with the radical $R_3$, and the radical $R_1''$ forms together with the radical $R_4$, an alkylene group having the structure $$-(CH_2)_z-,$$

so that the corresponding hexacarboxylic acid hexa-amides of formula VIII have a tricyclic structure; or, the radical $R_1'$ forms together with the radical $R_3''$, a corresponding alkylene group having the above-stated structure. Also, in the monocyclic, dicyclic, tricyclic or polycyclic compounds of formula VIII, z is an integer of 4-15, preferably 5-14, most preferably 6-12, in the groups of formula $$-(CH_2)_z-.$$

Optionally, there can be present in the corresponding divalent organic radicals such substituents which do not have more hydrophilic properties, e.g. halogen atoms.

Accordingly, hexacarboxylic acid hexa-amides of formula II which are particularly preferred complex-forming agents for magnesium ions correspond to the above-stated formula III

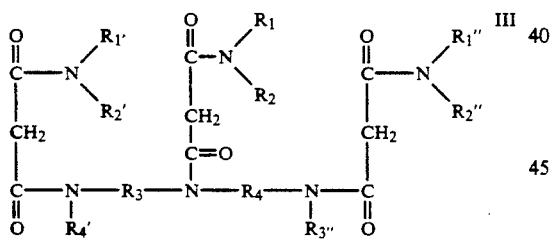

wherein the radicals $R_3$ and $R_4$ are groups having the structure $$-(CH_2)_n-$$

in which
n is an integer in the range of 5-9,
$R_4'$ and $R_3''$ are independently from each other hydrogen or alkyl radicals having 1-4 carbon atoms,
$R_1$, $R_1'$ and $R_1''$ are hydrogen or alkyl groups having 1-12 carbon atoms; or
the radical $R_1$ forms together with the radical $R_1'$ an alkylene group, and/or the radical $R_2$ forms together with the radical $R_1''$ an alkylene group, which alkylene groups have the structure $$-(CH_2)_z-,$$

in which z is an integer of 5-9, and wherein the corresponding remaining radicals which do not form the above-defined alkylene groups are hydrogen atoms or alkyl groups having 1-12 carbon atoms.

Of the hexacarboxylic acid hexa-amides of formula VIII, preferred are those lipophilic complex-forming agents for magnesium ions which correspond to the following formula IX

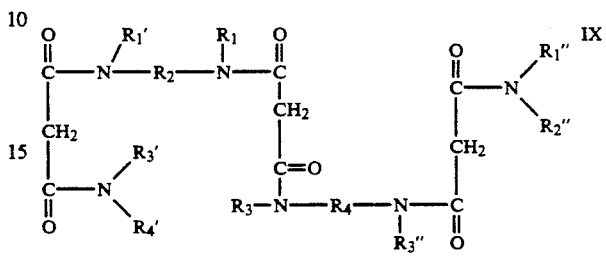

wherein the radicals $R_2$ and $R_4$ are, independently from each other, groups having the structure $$-(CH_2)_n-$$

in which
n is an integer in the range of 5-9,
$R_1'$ and $R_3$ are independently from each other hydrogen or alkyl radicals having 1-4 carbon atoms,
$R_3'$ and $R_1''$ are alkyl radicals having 5-9 carbon atoms, and
$R_4'$, $R_1$, $R_3''$, $R_1'$ and $R_2'$ are hydrogen or alkyl groups having 1-12 carbon atoms, or
the radical $R_3'$ forms together with the radical $R_1'$ an alkylene group; and/or the radical $R_4'$ forms together with the radical $R_2''$ an alkylene group; or the radical $R_3$ forms together with the radical $R_1'$, or together with the radical $R_2''$, or together with the radical $R_1''$, an alkylene group, which alkylene groups have the structure $$-(CH_2)_z-,$$

in which
z is an integer of 5-9; and wherein the corresponding remaining radicals which do not form the above-defined alkylene groups are hydrogen atoms or alkyl groups having 1-12 carbon atoms.

Preferred lipophilic magnesium complexes are the lipophilic 1:1 magnesium complexes of the above-stated preferred hexacarboxylic acid hexa-amides having the structures III and IX, respectively.

The hexacarboxylic acid hexa-amides which form the new lipophilic complexes with magnesium ions can be prepared according to methods which are familiar to those persons experienced in the art. For instance, the corresponding reactive derivatives of carboxylic acids, e.g. active carboxylic acid esters, carboxylic acid anhydrides or carboxylic acid halides, can be reacted with corresponding amines, to yield the desired hexacarboxylic acid hexa-amides.

For example, the preferred hexacarboxylic acid hexaamides of formula II

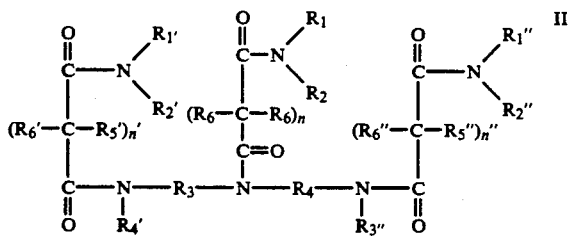

in which the radicals $R_3$ and $R_4$ have independently from each other the meaning of divalent aliphatic, alicyclic, aromatic, heteroaromatic or combinations of said radicals, and the radicals $R_1$, $R_2$, $R_5$, $R_6$, $R_1'$, $R_2'$, $R_4'$, $R_5'$, $R_6'$, $R_1''$, $R_2''$, $R_4''$, $R_5''$, $R_6''$, as well as n, n' and n'', are as defined above with regard to formula II, can be prepared by reacting a triamine of formula IV

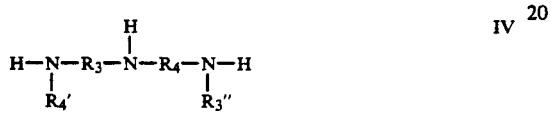

with carboxylic acids which correspond to the following formulae Va, Vb and Vc

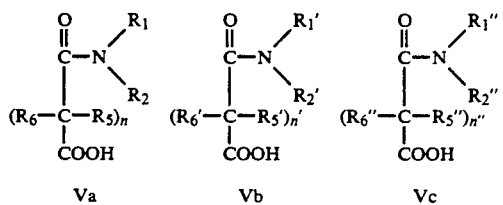

or reactive derivatives of said carboxylic acids yielding the corresponding hexacarboxylic acid hexa-amides of formula II.

The hexacarboxylic acid hexa-amides of formula II can be also prepared by reacting the amine having the formula IV first with dicarboxylic acids having the formulae VI, VIa and VIb

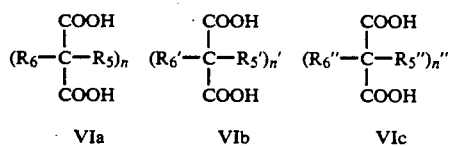

or with reactive derivatives of said dicarboxylic acids in which one of the dicarboxylic acid groups is optionally present in a protected form, to yield the corresponding intermediate product of formula VII

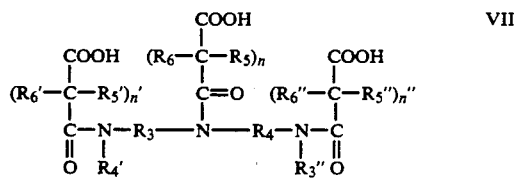

The corresponding intermediate product of formula VII, or a reactive derivative of said intermediate product, is thereafter reacted with a corresponding amine yielding the desired final product of formula II.

If the particularly preferred hexacarboxylic acid hexa-amides of formula III are prepared according to the first process outlined above, then the corresponding triamine of formula IV is reacted with a monoamide of malonic acid or a reactive derivative thereof, such as for instance the mono-4-nitrophenylester of malonic acid amide, to yield the corresponding final product of formula III. The preparation can be performed, for example, in a manner analogous to the method described for the tetracarboxylic acid tetra-amides of formula C in the publication of M. Muller et al. in *Mikro Chimica Acta*, 1989, pages 284 and 285, discussed above.

The preferred hexacarboxylic acid hexa-amides of formula VIII

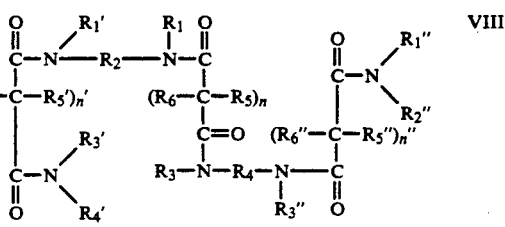

in which the substituents and symbols are as defined above, are preferably prepared by reacting two amino compounds which have the structure

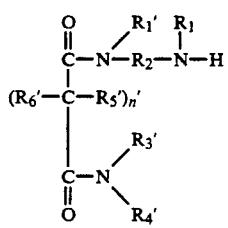

and

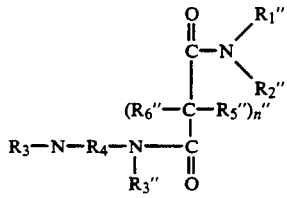

with a dicarboxylic acid having the structure

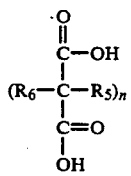

or a reactive derivative of said dicarboxylic acid, yielding the desired hexacarboxylic acid hexa-amides of formula VIII. If reactive derivatives of dicarboxylic acids are used to prepare the corresponding formula VIII compounds (for instance corresponding dicarboxylic acid halides), then the reaction is preferably performed in the presence of a base which neutralizes the hydrohalic acid liberated during the reaction.

A further object of the present invention is a test device, or an ion-selective part for the determination of the concentration or the activity of magnesium ions in liquid samples. The test device or ion-selective part contains a hexacarboxylic acid hexa-amide as the magnesium-selective component.

Preferred inventive test devices (e.g., test strips) and ion-selective parts contain as hexacarboxylic acid hexaamides, the preferred hexacarboxylic acid hexa-amides which have in their molecular structures three dicarboxylic acid diamide moieties corresponding to the formulae I, I' and I'', in which formulae the corresponding substituents have the meaning stated above.

Particularly preferred hexacarboxylic acid hexaamides which are contained in the ion-selective parts are the hexacarboxylic acid hexa-amides having the formulae II and VIII stated above. Still more preferred are those ion-selective parts which contain as the ion-selective component the particularly preferred hexacarboxylic acid hexa-amides having the formulae III and IX respectively.

The corresponding ion-selective parts can be used in order to determine the concentration, or the activity, of magnesium ions in sample solutions, e.g. aqueous sample solutions. It is possible, using the inventive hexacarboxylic acid hexa-amides, to prepare corresponding ion-selective parts which have sufficiently high selectivity for magnesium ions over calcium ions and sodium ions so that the corresponding ion-selective parts can be used for the determination of magnesium ions in biological materials, like body fluids such as urine, blood serum or whole blood.

About 1.1 millimolar of calcium ions are usually present in human blood serum in free form. 0.6 millimolar magnesium ions are present as well, in free form. Further quantities of calcium ions and magnesium ions are present in blood serum in bonded form, i.e. bonded to protein molecules. The quantity of magnesium ions which are present in the blood serum in free form depends on the pH of the blood serum. When the pH increases further, the magnesium ions which are present in free form become bonded to protein molecules. The quantity of free magnesium ions is thus reduced through an increase in pH.

Magnesium-containing pharmaceutical preparations are administered in order to mitigate several undesired conditions. A prophylactic treatment with magnesium-containing pharmaceutical preparations may also be performed. For instance, magnesium-containing pharmaceutical preparations are administered in order to mitigate cramps and lower the risk of cardiac infract. Furthermore, it has been found that if pharmaceutical preparations containing magnesium ions are administered to pregnant women, the risk of an abortion may be lowered.

If magnesium ions are administered to human beings in need of such treatment, then it is necessary to monitor the magnesium content of the blood in order to observe the reaction of the treated person to the magnesium therapy.

It is possible to use the inventive ion-selective parts which contain as the ion selective component a hexacarboxylic acid hexa-amide, preferably the preferred hexacarboxylic acid hexa-amides defined above, for the determination of the concentration, and activity, of magnesium ions in solutions which have a rather low pH, e.g. a pH value of about 5. Because of the good selectivity of the corresponding ion-selective members for magnesium ions over calcium ions, the inventive ion-selective members can be used for the determination of magnesium-hardness of water samples. The magnesium concentration can also be determined in biological materials, such as body fluids. In as far as the determination of the free magnesium ions in blood and blood serum is concerned, the determination can be performed without shifting the pH value of the blood serum to the basic range by adding base. Because of this, the ratio of free magnesium ions is not shifted in the blood serum due to the addition of a base.

The preparation of ion-selective parts using an ion-selective component which has a selectivity for the anion to be determined, or the cation to be determined, is well known in the art. Usually such ion-selective parts contain the ion selective component embedded in a matrix of a polymeric material. The ion-selective parts usually contain a plasticizer. Sometimes ion exchangers are furthermore present. The inventive ion-selective parts which have a selectivity for magnesium ions contain the lipophilic magnesium-selective hexacarboxylic acid hexa-amides, preferably embedded in a polymeric material. Preferred polymeric materials are homopolymers or copolymers of vinyl halides, or homopolymers or copolymers of vinylidene halides. Particularly preferred are homopolymers or copolymers of vinyl chloride. Even more preferred are polyvinylchloride homopolymers.

Usually, the ion-selective parts additionally contain a plasticizer, preferably a plasticizer having sufficiently high lipophilic properties.

Examples of plasticizers which may be used in the inventive ion-selective members, are ether plasticizers, e.g. o-nitro-phenyl-octylether, and ester plasticizers. Dicarboxylic acid diesters or tetracarboxylic acid tetraesters are preferred. Examples of dicarboxylic acid esters are the esters of sebacic acid or adipic acid. Examples of tetracarboxylic acid tetraesters are the esters of benzophenone tetracarboxylic acids and benzhydrol tetracarboxylic acids. The alcohol component of the ester plasticizers is usually an aliphatic alcohol having an alkyl chain of at least 5 carbon atoms, e.g. an alkyl chain of 5–15 carbon atoms.

Optionally, the inventive ion selective parts contain as a further component, an ion exchanger, e.g. a tetraphenyl borate which has optionally in its benzene nucleus further substituents. Examples of such anion exchanges are p-chlorotetraphenyl borate and salts thereof.

Particularly preferred inventive ion-selective parts, e.g. ion-selective membranes for ion selective electrodes, have the following composition:

0.1–2 parts by weight of the magnesium selective hexacarboxylic acid hexa-amide,
28–38 parts by weight of polyvinylchloride, and
61–71 parts by weight of plasticizer.

If the ion-selective membranes contain as a further component an ion exchanger, for example the above-stated tetraphenyl borate or a salt thereof, then per 100 mol-% of the corresponding magnesium selective hexacarboxylic acid hexa-amide, there are present preferably 70 mol-% to 170 mol-% of said ion exchanger, most preferably 90 mol-% to 150 mol-%.

Corresponding test devices, e.g. test strips, for the determination of magnesium ions in sample solutions, contain the magnesium-selective hexacarboxylic acid hexa-amide embedded in a carrier material, for instance a polymeric material. Usually the test devices contain as a further component an indicator, e.g., a pH indicator, which changes optical properties due to protons which are liberated when the complex between magnesium selective hexacarboxylic acid hexa-amide and magnesium ions is formed.

The present invention is further illustrated through the following non-limitative examples.

EXAMPLE 1

A hexacarboxylic acid hexa-amide was prepared corresponding to the above preferred formula III. Each of the divalent radicals $R_3$ and $R_4$ was a group having the structure —$(CH_2)_n$— in which n was 6, $R_4'$ and $R_3''$ were hydrogen atoms, each of the radicals $R_1$, $R_1'$ and $R_1''$ was a heptyl radical, and each of the radicals $R_2$, $R_2'$ and $R_2''$ was a methyl group.

The new hexacarboxylic acid hexa-amide accordingly corresponded to the following formula IIIa

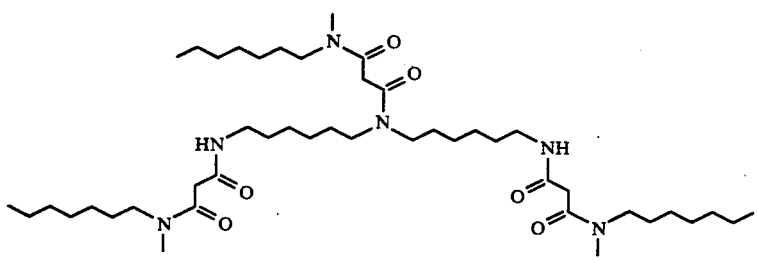

Reaction Step A

Preparation of the 4-nitrophenyl ester of a malonic acid amide in which the amide forming amine is n-heptyl-methylamine.

The above active ester of malonic acid amide was prepared from malonic acid monomethyl ester chloride and n-heptyl-methylamine. The corresponding methylester of the stated malonic acid amide was formed as an intermediate. The methylester was saponified to yield the free acid, and finally esterified with 4-nitrophenol in the presence of N,N-dicyclohexylcarbodiimide to yield the active ester of the title malonic acid amide.

Further details concerning the preparation of the aforesaid intermediate product are disclosed on pages 284 and 285 of M. Muller, R. Rouilly, B. Rusterholz, M. Maj-Zurawska, Z. Hu and W. Simon, *Microchim. Acta* [Vienna], III, 1988, which was mentioned above.

Reaction Step B

Preparation of the hexacarboxylic acid hexa-amide of formula IIIa.

The triamine of formula

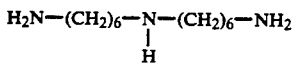

is available from the Aldrich Company, U.S.A.

The triamine was reacted with the active ester of the malonic acid monoamide prepared according to step A in a mol ratio of 1:3. The reaction was performed using toluene as the solvent. At the beginning, the reaction mixture was stirred for 30 minutes at room temperature and thereafter heated to a temperature of 110° C. and maintained at that temperature for one hour.

After cooling the reaction mixture to room temperature, the organic layer was washed with a 0.1 normal aqueous sodium hydroxide solution, dried and thereafter evaporated under vacuum. The remaining residue was purified through flash chromatography on a silicagel column. The eluent was a mixture of 4 volumes of methylene chloride and one volume of acetone. The yield corresponded to 16% of the theoretical yield.

The elemental analysis of the final product gave the following values: calculated: C=66.96, H=10 74, N=10.41; found: C=66.69, H=10.84, N=10.39.

The IR spectrum in $CHCl$: showed peaks at 3290, 1662 and 1627 $cm^{-1}$.

The MS yielded: 807 (6% $(M+1)^+$, 198 (11%), 156 (18%), 128 (18%).

The NMR spectrum gave the following results:

$^1H$-NMR (300 MHz, $CDCl_3$): 0.82–0.94 (m, 9H, 3($CH_2$)$_6$ C$H_3$); 1.18–1.42 (M, 32H, 16 $CH_2$); 1.42–1.64 (m. 14H, 7 NC$H_2$CH$_2$); 2.925, 2.942, 2.944, 3.022, 3.049 (5s, 9H, 3 NC$H_3$); 3.18–3.41 (m, 18H, 2 HNCOC$H_2$, 2HNC$H_2$, 2 NC$H_2$, 3 CH$_3$NC$H_2$); 3.45 (s, 2H, NCOC$H_2$); 7.88–7.98 (br, 1H, NH); 7.98–8.08 (br, 1H, NH).

The following Examples 2 and 3 illustrate inventive magnesium selective membranes, and the results achieved with such membranes.

EXAMPLE 2

Preparation of Ion-Selective Membranes

Ion-selective membranes were prepared using the hexacarboxylic acid hexa-amides prepared according to Example 1. The preparation of the membranes was performed according to the process which is described in the publication of U. Oesch, Z. Brzozka, A. Xu, B. Rusterholz, G. Suter, H.-V. Pham, D. H. Welti, D. Ammann, E. Pretsch and W. Simon in *Anal. Chem.* 1986, 58, 2284.

The ion-selective membranes had the composition stated in the following table:

| Constituent | % by weight |
|---|---|
| hexacarboxylic acid hexa-amide | 1 |
| polyvinylchloride | 33 |
| plasticizer | 66 |

The plasticizer was o-nitro-phenyl octylether. The membranes prepared for testing either contained no ion exchanger or they contained as the ion exchanger a potassium salt of tetraphenyl borate in which each of the four benzene nuclei had a chlorine substituent in the para position.

Membranes were prepared which contained, per 100 mol-% of the hexacarboxylic acid hexa-amide, the following amounts of ion exchanger: 0 mol-%, 40 mol-%, 70 mol-%, 90 mol-%, 120 mol-%, 150 mol-%, and 170 mol-%.

EXAMPLE 3

EMF-measurements Using Ion-Selective Membranes

Magnesium-selective electrodes were prepared using the magnesium selective membranes prepared according to Example 2. The internal reference electrode of the magnesium-selective electrode was silver/silver chloride. The internal filling solution of the electrode was a solution containing several salts. The external reference was a calomel electrode.

EMF determination was performed with the following cell assembly:

Hg; Hg$_2$Cl$_2$; KCl (sat.)/3M KCl/sample solution/membrane/internal electrode filling, AgCl; Ag.

The internal electrode filling contained, per liter, 0.14 mols of sodium chloride, $4 \times 10^{-3}$ mols of potassium chloride, $10^{-3}$ mols of calcium chloride and $6 \times 10^{-4}$ mols of magnesium chloride.

$10^{-1}$ molar aqueous solutions of the corresponding metal chlorides were used for selectivity coefficient determination. The results of these tests are illustrated in FIG. 1. The selectivity factors expressed in $$\log K_{MgM}^{Pot}$$

are plotted on the ordinate. Plotted on the abscissa is the mol-% of the ion exchanger present in the membrane, (potassium salt of the tetrakis-(p-chlorophenyl)borate) per 100 mol-% of the hexacarboxylic acid hexa-amide.

It can be seen from the FIG. that the membranes which contain 90 mol-%, 120 mol-%, 150 mol-% of the stated tetraphenyl borate potassium salt had a higher selectivity for magnesium ions than for the alkaline earth metal ions calcium and barium. The membranes furthermore had a higher selectivity for magnesium ions over all alkali metal ions, and also over ammonium ions. It furthermore can be seen from FIG. 1 that particularly good results are achieved with membranes which contain 120 mol-% and 150 mol-%, respectively, of the stated cation exchanger, per 100 mol-% of the ion-selective hexacarboxylic acid hexa-amide. The membrane exhibited a clearly higher selectivity for magnesium ions than for calcium ions, and an extremely high selectivity for magnesium ions over sodium ions. The very high selectivity for magnesium ions over sodium ions is of great importance. In biological materials, such as body fluids, far higher concentrations of sodium ions than magnesium ions are present.

The present test results may be compared to results which were achieved with membranes containing an amino-substituted succinic acid diamide as the ion selective component. The prior art test results are illustrated on page 2015 of M. V. Rouilly, M. Badertscher, E. Pretsch, G. Suter and W. Simon, *Analytical Chemistry*, vol. 60, 19, October 1988, mentioned above. It can be clearly seen that the new inventive hexacarboxylic acid hexa-amides have a far higher selectivity for magnesium ions over sodium ions than the amino-substituted succinic acid diamide described in the prior art. Using the inventive hexacarboxylic acid hexa-amides, it is possible to determine the magnesium concentration, and the magnesium activity, in sample solutions which have a neutral or even weakly acidic pH value. This result is of extraordinary importance. Contrary to this, with the ion selective membranes described in the above-stated Rouilly et al. publication, it was only possible to determine the magnesium concentrations in sample solutions which have a pH value in the range of 8-9.

The pH value of the sample solutions, the test results of which are illustrated in the FIG. was about 6. Contrary to this, the sample solutions from which the test results illustrated on page 2015 of Rouilly et al. were obtained had a pH value of 8.8.

The plasticizer was p-nitrophenyl octylether in the inventive membranes. This plasticizer is well suited for membranes intended for use in the determination of blood serum ion concentrations.

The tetracarboxylic acid tetraamides which are described in the publication of M. Muller, M. Rouilly, B. Rusterholz, M. Maj-Zurawska, Z. Hu and W. Simon in *Mikrochim. Acta* [Vienna], III, pages 283-290, 1988, mentioned above, have low solubility. It is therefore necessary to include chloroparaffin as a plasticizer in membranes containing those tetracarboxylic acid tetraamides. Ion-selective membranes which contain a chloroparaffin as a plasticizer are not suited for blood serum ion concentration determination.

EXAMPLE 4

Further hexacarboxylic acid hexa-amides corresponding to formula III were prepared according to the process described in Example 1. The new hexacarboxylic acid hexa-amides had the following structural formulae A-J:

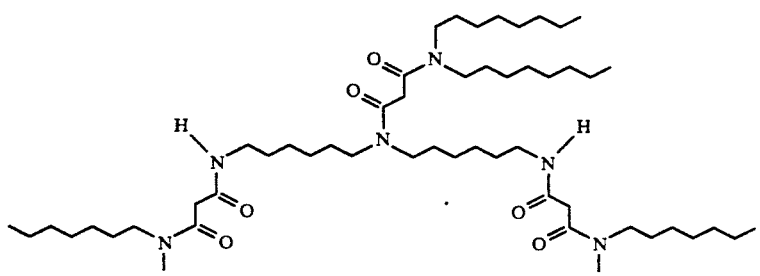

A

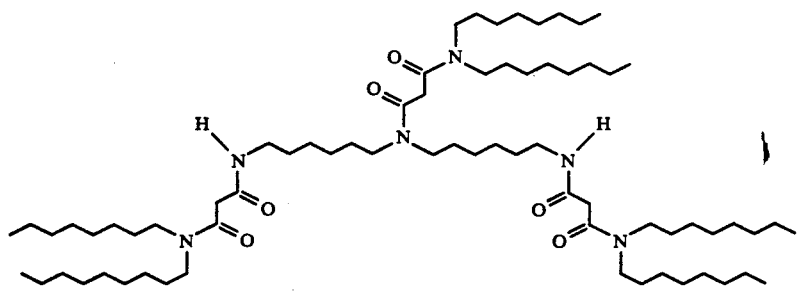
B
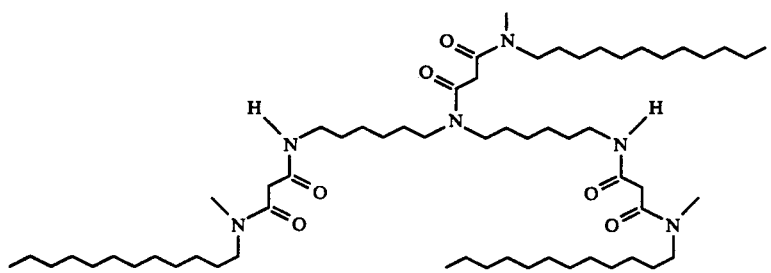
C
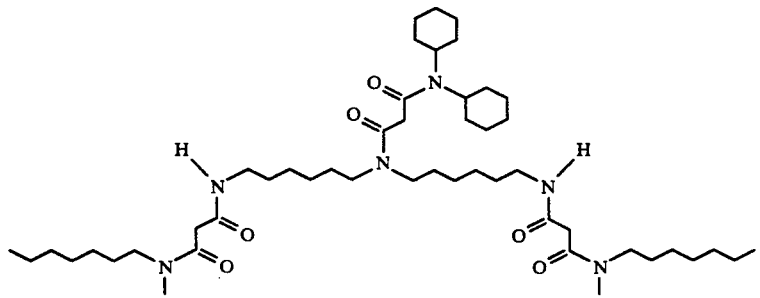
D
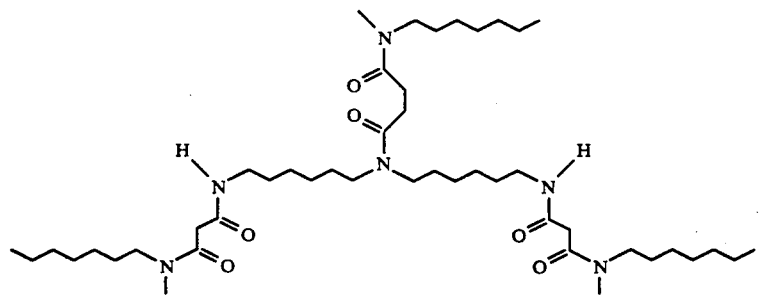
E
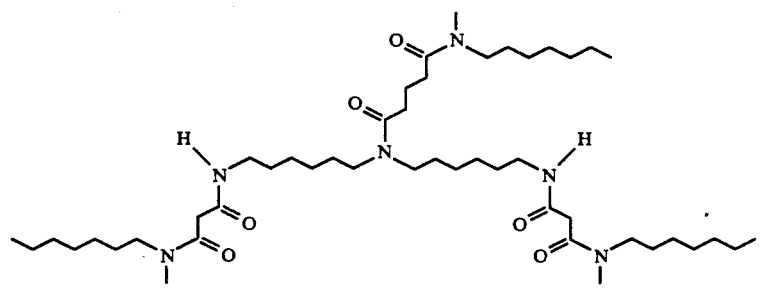
F

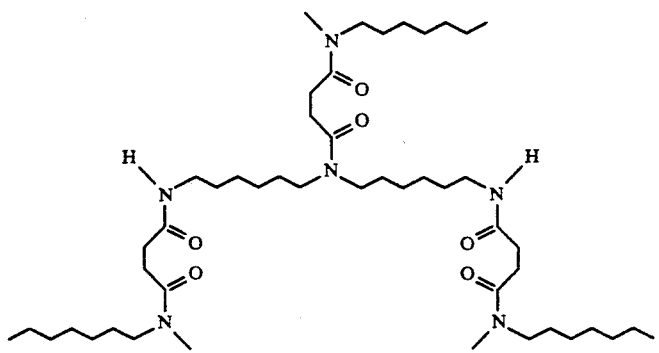

G

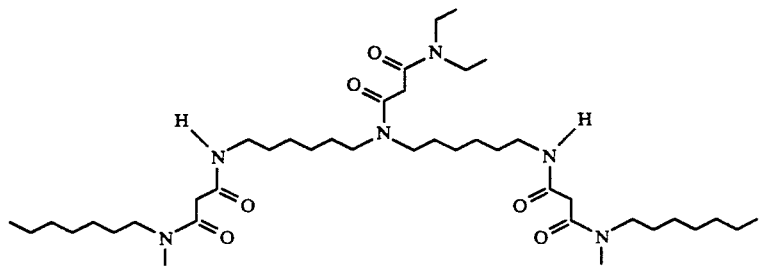

H

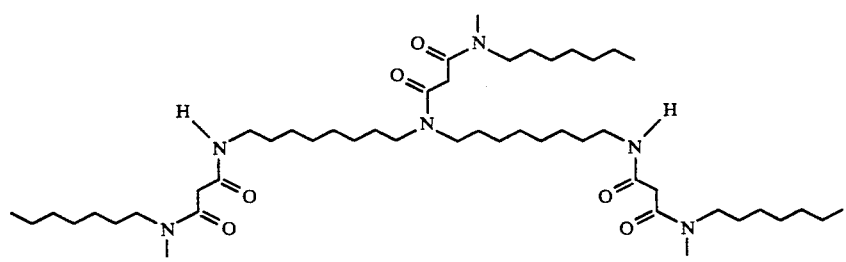

J

EXAMPLE 5

The preparation of preferred hexacarboxylic acid hexa-amides of formulae VIII and IX is illustrated by hexa-amides having structural formulae K and L.

amines with a reactive dicarboxylic acid derivative, i.e. with malonic acid dichloride (preparation of compound K) or with succinic acid dichloride (preparation of compound L).

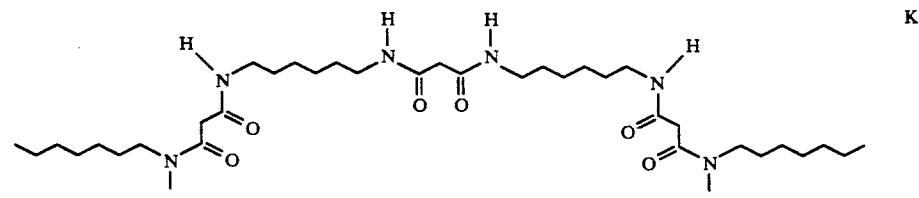

K

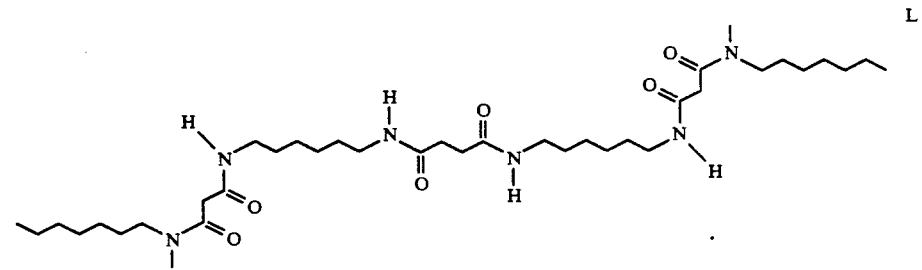

L

Compounds K and L were prepared according to the process outlined above, i.e. by reacting corresponding The reaction between dicarboxylic acid dichloride and the amine was performed in methylene chloride solvent, in the presence of triethylamine as an agent for neutralizing the hydrochloric acid formed during the reaction. The amines and the triethylamine were dissolved in methylene chloride. Dicarboxylic acid diamine dissolved in methylene chloride was added to the cooled solution.

Two further hexacarboxylic acid hexa-amides were prepared according to the above process. They were structurally closely related to the compounds of formulae K and L, respectively. The further hexacarboxylic acid hexa-amides, however, differed from the compounds of formulae K and L in that the amide-forming amine at the two end positions (which is n-heptyl methylamine in the case of the formulae K and L compounds) was di-n-octyl amine.

EXAMPLE 6

Ion selective membranes according to the process described in Example 2 were prepared from the ion-selective components described in Examples 4 and 5. EMF determination were performed in cells of the type described in Example 3.

The test showed that the compounds of structural formulae A, C, D, E and H (Example 4), and compound L (Example 5), had a selectivity similar to the Example 1 compound for magnesium ions over calcium ions, and for magnesium ions over sodium ions.

The formula J compound, described in Example 4, had the highest selectivity for magnesium ions over calcium ions. A membrane containing 150 mol-% of the above-stated chloro-substituted tetraphenyl borate potassium salt, per 100 mol-% of the formula J compound, had a selectivity for magnesium ions over calcium ions of −1.0, i.e. the value $$\log K_{MgCa}^{Pot}$$

was −1.0. This membrane furthermore had a very high selectivity for magnesium ions over sodium ions i.e. the corresponding value of $$\log K_{MgNa}^{Pot}$$

was −2.8.

What is claimed is:

1. A hexacarboxylic acid hexa-amide adapted for forming lipophilic complexes with magnesium ions, and lipophilic complexes of said hexacarboxylic acid hexa-amide with magnesium ions, said hexacarboxylic acid hexa-amide having the following formula II:

[Formula II structure]

wherein
(i) $n$, $n'$ and $n''$ are independently 1 or 2,
(ii) $R_1$ and $R_2$ are independently selected from the group A, consisting of hydrogen, $C_1$–$C_{15}$ alkyl, $C_2$–$C_{15}$ alkenyl, $C_2$–$C_{15}$ alkynyl, cyclohexyl and phenyl;
(iii) $R_1'$ and $R_2'$ are independently selected from the group A defined above;
(iv) $R_1''$ and $R_2''$ are independently selected from group A as defined above;
(v) $R_3$ is selected from the group B consisting of a divalent aliphatic, alicyclic and aromatic hydrocarbon radicals;
(vi) $R_3''$ is selected from group A defined above;
(vii) $R_4$ is selected from group B defined above;
(viii) $R_4'$ is selected from group A defined above;
(ix) $R_5$, $R_5'$, $R_5''$, $R_6$, $R_6'$ and $R_6''$ are independently selected from the group consisting of hydrogen, $C_1$–$C_4$ alkyl and halogen.

2. A hexacarboxylic acid hexa-amide according to claim 1 and complexes thereof with magnesium ions wherein $R_4$ is a divalent aliphatic hydrocarbon radical having the formula $$-(CH_2)_z-,$$

$R_3$ is a divalent alkylene group of the formula $$-(CH_2)_z-,$$

and $z$ is an integer from 4 to 15.

3. A hexacarboxylic acid hexa-amide or magnesium complex thereof according to claim 1 which contains at least one alkyl, alkenyl or alkynyl group containing 4–15 carbon atoms.

4. A hexacarboxylic acid hexa-amide or magnesium complex thereof according to claim 2, said hexa-amide having the formula III

[Formula III structure]

wherein
$R_3$ and $R_4$ are independently alkylene groups of the formula $$-(CH_2)_z-$$

in which $z$ is an integer from 5 to 12,
$R_3''$ and $R_4'$ are independently hydrogen or $C_1$–$C_4$ alkyl,
$R_1$, $R_1'$ and $R_1''$ are independently $C_5$–$C_9$ alkyl, and $R_2$, $R_2'$ and $R_2''$ are independently hydrogen or $C_1$–$C_{12}$ alkyl.

5. A hexacarboxylic acid hexa-amide adapted for forming lipophilic complexes with magnesium ions, and lipophilic complexes of said hexacarboxylic acid hexa-amide with magnesium ions, said hexacarboxylic acid hexa-amide having the following formula VIII

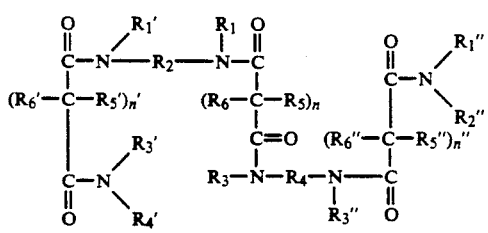

wherein (i) n, n' and n" are independently 1 or 2,
(ii) $R_1$, $R_1'$, $R_3$ and $R_3''$ are independently selected from the group A consisting of hydrogen, $C_1$-$C_{15}$ alkyl, $C_2$-$C_{15}$ alkenyl, $C_2$-$C_{15}$ alkynyl, and cyclohexyl and phenyl;
(iii) $R_2$ and $R_4$ are independently selected from the group B consisting of divalent, aliphatic, alicyclic and aromatic hydrocarbon radicals,
(iv) $R_1''$ and $R_2''$ are independently selected from the group A as defined above;
(v) $R_3'$ and $R_4'$ are independently selected from group A defined above; and
(vi) $R_5$, $R_5'$, $R_5''$, $R_6$, $R_6'$ and $R_6''$ are independently selected from the group consisting of hydrogen, $C_1$-$C_4$ alkyl and halogen.

6. A hexacarboxylic acid hexa-amide according to claim 5 and complexes thereof with magnesium ions wherein $R_4$ is a divalent aliphatic hydrocarbon radical having the formula $$-(CH_2)_z-,$$

$R_3$ is a divalent alkylene group of the formula $$-(CH_2)_z-,$$

and z is an integer from 4 to 15.

7. A hexacarboxylic acid hexa-amide or magnesium complex thereof according to claim 5 which contains at least one alkyl, alkenyl or alkynyl group containing 4-15 carbon atoms.

8. A hexacarboxylic acid hexa-amide or magnesium complex thereof according to claim 6, said hexa-amide having the formula IX

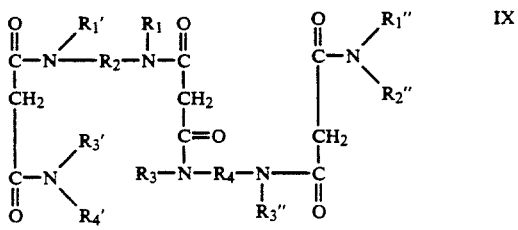

wherein $R_2$ and $R_4$ are independently selected from alkylene groups having the formula $$-(CH_2)_z-$$

in which z is an integer from 5-12, $R_1$, $R_2''$, $R_3''$ and $R_4'$ are independently selected from hydrogen and $C_1$-$C_{12}$ alkyl, $R_1'$ and $R_3$ are independently selected from hydrogen and $C_1$-$C_4$ alkyl, and $R_1''$ and $R_3'$ are independently selected from $C_5$-$C_9$ alkyl.

* * * * *